(12) United States Patent
Hahn et al.

(10) Patent No.: US 6,534,076 B1
(45) Date of Patent: Mar. 18, 2003

(54) STABILIZED ISOTHIAZOLONE COMPOSITIONS AND METHODS OF STABILIZATION OF ISOTHIAZOLONE

(75) Inventors: Soon-Jong Hahn, Seoul (KR); Jin-Man Kim, Kyungki-do (KR); Ki-Seung Choi, Kyungsangbuk-do (KR); Seung-Hwan Kim, Kyungki-do (KR); Jung-Ho Park, Kyungki-do (KR); Jae-Min Ha, Kyungki-do (KR); Gi-Bae Kim, Kyungki-do (KR)

(73) Assignee: SK Chemicals (KR)

( * ) Notice: Subject to any disclaimer, the term of this patent is extended or adjusted under 35 U.S.C. 154(b) by 0 days.

(21) Appl. No.: 09/586,874

(22) Filed: Jun. 5, 2000

(30) Foreign Application Priority Data

Dec. 31, 1999 (KR) .............................................. 99-67757
May 22, 2000 (KR) ........................................ 2000-27455

(51) Int. Cl.$^7$ .............................................. A01N 25/02
(52) U.S. Cl. ...................... 424/405; 504/156; 514/372; 548/213; 510/383
(58) Field of Search ................................. 514/372, 483; 424/405, 713, 601, 605, 56, 57, 76.8, 78.07, 78.09; 548/213; 504/156, 148; 510/382, 383

(56) References Cited

U.S. PATENT DOCUMENTS

| 3,870,795 | A |   | 3/1975 | Miller et al. ................. 424/270 |
| 4,067,878 | A |   | 1/1978 | Miller et al. ................. 260/302 |
| 4,173,643 | A | * | 11/1979 | Law ........................... 424/270 |
| 5,741,483 | A | * | 4/1998 | Okawa ...................... 424/78.09 |

* cited by examiner

*Primary Examiner*—Neil S. Levy
(74) *Attorney, Agent, or Firm*—Gifford, Krass, Groh, Sprinkle, Anderson & Citkowski, P.C.

(57) ABSTRACT

The present invention relates to stabilized isothiazolone compositions and methods of stabilization of isothiazolone, more particularly, to stabilized isothiazolone solutions comprising (a) an isothiazolone composition, (b) sulfuric acid, and (c) solvent.

3 Claims, No Drawings

STABILIZED ISOTHIAZOLONE COMPOSITIONS AND METHODS OF STABILIZATION OF ISOTHIAZOLONE

BACKGROUND OF THE INVENTION (a) Field of the Invention

The present invention relates to a stabilized isothiazolone composition and a method of stabilization of isothiazolone, more particularly, to a stabilized isothiazolone solution comprising (a) an isothiazolone compound of formula I, (b) sulfuric acid, and (c) solvent.

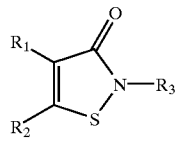

(I)

where $R_1$ and $R_2$ each independently represent a hydrogen atom, a halogen atom, or $C_1$–$C_4$ alkyl group, or $R_1$ and $R_2$ together form a cyclic allyl group;

$R_3$ represents a hydrogen atom; $C_1$–$C_{10}$ alkyl group which is substituted or unsubstituted with a halogen atom or hydroxy group, $C_2$–$C_{10}$ alkenyl group which is substituted or unsubstituted with a halogen atom, $C_2$–$C_{10}$ alkynyl group which is substituted or unsubstituted with a halogen atom, $C_1$–$C_{10}$ alkyl group, or aralkyl group which is substituted or unsubstituted with $C_2$–$C_9$ alkoxy group.

The present invention also relates to a method of stabilization of isothiazolone of the formula I.

(b) Description of the Related Art

Since development by Craw et al. in 1965, isothiazolone compounds have been extensively used in many industrial fields as a disinfectant including an antibacterial and antimicrobial agent for dyes, cosmetics, fibers, or plastics, etc.

However, since isothiazolone is very unstable and easily degraded by moisture in the air, heat and ultraviolet light, the beneficial properties of the compound may be lost during storage. In order to improve the stability of isothiazolone, several methods have been actively developed, and the typical method is to use a metal salt stabilizer.

In U.S. Pat. Nos. 3,870,795 and 4,067,878, for example, metal nitrite or metal nitrate are added to stabilize isothiazolone solutions. But such metal salt stabilizers react with emulsion components in a latex emulsion to produce precipitates. Further, in some cases, chlorine ions in the metal salt may induce corrosion of the system and metal ions may increase the hardness of water to induce scale. Thus, in such cases, the use of the metal salt is undesirable.

A preferred disinfectant should be stable during use, but should be quickly degraded after use so as not to cause a persistent environmental problem. Accordingly, there is a need for a stabilizer satisfying these requirements.

SUMMARY OF THE INVENTION

A stabilized isothiazolone solution is provided that is useful as a disinfectant and antimicrobial agent, has high stability and can contain active ingredient in high concentration.

A method of stabilization of isothiazolone is also provided which can stabilize an isothiazolone longer than the conventional method using ferric salt, substantially prevents the formation of nitrosamine and precipitates, substantially prevents heavy metals from being discharged to the environment, substantially prevents ions such as $Mg^{2+}$ from binding to ions contained in the industrial water such as $PO_4^{3-}$, $CO_3^{2-}$ to form a Hard Scale and does not use stabilizers comprising ferric salts.

The present invention provides a stabilized isothiazolone composition comprising (a) an isothiazolone of formula I, (b) sulfuric acid, and (c) solvent.

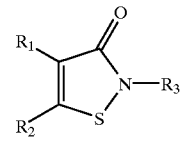

(I)

where $R_1$ and $R_2$ each independently represent a hydrogen atom, a halogen atom, or a $C_1$–$C_4$ alkyl group, or $R_1$ and $R_2$ together form a cyclic allyl group;

$R_3$ represents a hydrogen atom, $C_1$–$C_{10}$ alkyl group which is substituted or unsubstituted with a halogen atom or hydroxy group, $C_2$–$C_{10}$ alkenyl group which is substituted or unsubstituted with a halogen atom, $C_2$–$C_{10}$ alkynyl group which is substituted or unsubstituted with a halogen atom, $C_1$–$C_{10}$ alkyl group, or aralkyl group which is substituted or unsubstituted with $C_2$–$C_9$ alkoxy group.

The present invention also provides a method of stabilization of isothiazolone comprising stabilizing isothiazolone by blending an isothiazolone and a stabilizer, where the isothiazolone is that of formula I, and the stabilizer is sulfuric acid.

The present invention also provides a method of sterilization of bacteria and/or fungi and/or algae or suppression of the growth thereof comprising applying disinfectant compositions in the area that is contaminated or contamination-vulnerable by bacteria and/or fungi and/or algae, wherein said disinfectant compositions are the stabilized isothiazolone solutions comprising (a) isothiazolone compound represented by the formula I, (b) sulfuric acid and (c) solvent.

DETAILED DESCRIPTION AND THE PREFERRED EMBODIMENTS

Upon having endeavored to solve the problem of the conventional method of stabilization of isothiazolone, the present invention utilizes sulfuric acid as a stabilizer. Thus, the degradation of isothiazolone can be inhibited, and even completely prevented according to the present invention.

The stabilized isothiazolone solution of the present invention includes an isothiazolone compound represented by formula I, sulfuric acid and solvent.

The isothiazolone compound which may be used in the present invention illustratively includes one or more compounds selected from the group represented by formula 1, preferably one or more compounds such as 5-chloro-2-methyl-4-isothiazolin-3-one, 2-methyl-4-isothiazolin-3-one, 4,5-dichloro-2-methyl-4-isothiazolin-3-one, 5-chloro-2-n-octyl-4-isothiazolin-3-one, 4,5-dichloro-2-n-octyl-4-isothiazolin-3-one and benzoisothiazolin-3-one. It is more preferable to use 5-chloro-2-methyl-4-isothiazolin-3-one or 4,5-dichloro-2-methyl-4-isothiazolin-3-one alone or a mixture of 5-chloro-2-methyl-4-isothiazolin-3-one and 2-methyl-4-isothiazolin-3-one. When using a mixture of 5-chloro-2-methyl-4-isothiazolin-3-one and 2-methyl-4-isothiazolin-3-one, the weight ratio is preferably about 50:50–99:1, more preferably about 60:40–95:5. In addition, it is also preferable to use a mixture comprising 2-methyl-4-isothiazolin-3-one as an active ingredient and a small amount of 5-chloro-2-methyl-4-isothiazolin-3-one. In such case, the weight ratio is preferably about 99.5:0.5–90:10, more preferably about 98:2–96:4.

The sulfuric acid used as stabilizer in the stabilized isothiazolone solution of the present invention preferably is high purity, such as spectroscopic or reagent grades.

The solvent contained in the stabilized isothiazolone solution can be any type of solvent which can effectively disperse the isothiazolone compound and sulfuric acid. Preferably the solvent is water. The amount of solvent can be varied according to the use of the stabilized isothiazolone solution. And, if the purpose is only storage, the solvent may not be used.

The stabilized isothiazolone solution according to the present invention may be made in the form of concentrated solution or diluted solution according to the purpose. When stabilized isothiazolone is employed in exceptional cases such as mass shipments, more concentrated solutions may be used. The isothiazolone solution comprises about 0.00001–99 wt % of one or more compounds selected from isothiazolone represented by formula I, 0.00001–99 wt % of stabilizer, and less than 99.99998 wt % of solvent. Preferably, it comprises 0.1–40 wt % of one or more compounds selected from isothiazolone represented by formula I, 0.1–99 wt % of stabilizer, and 99.8 wt % or less of solvent. Most preferably, it comprises 1–30 wt % of one or more compounds selected from isothiazolone represented by formula I, 5–99 wt % of stabilizer, and 94 wt % or less of solvent. Conventional isothiazolone solution using metal salt stabilizer can contain at most 14 wt % of active ingredient isothiazolone, while the stabilized isothiazolone solution of the present invention can contain up to 40 wt % of isothiazolone.

The amount of stabilizer may vary according to the conditions of use and the concentration of isothiazolone in a mixture; preferably, the weight ratio of isothiazolone:stabilizer is in the range of 1:0.01–1:1,000. This range is preferable in terms of stability and cost-saving. In the case of a concentrated solution, the weight ratio of isothiazolone:stabilizer is preferably in the range of 1:0.02–1:50. Even though more amount of stabilizer may be used, this is uneconomical. In the case of an extremely diluted isothiazolone solution having about 1–10,000 ppm of isothiazolone in solvent, the weight ratio of isothiazolone:stabilizer is preferably in the range of 1:0.1–1:20, more preferably in the range of 1:0.1–1:10.

As aforementioned, the stabilized isothiazolone solution according to the present invention is very stable in the air, its efficacy may be sustained under a relatively prolonged period of time in storage, and it forms smaller precipitates than the conventional isothiazolone solution using metal salt stabilizer. Further, the stabilized isothiazolone solution according to the present invention exhibits excellent anti-microbial and biocidal activities when the effective amount of the solution is applied to the area that is contaminated or contamination-vulnerable by microbes, and removes the hard scale forming factor. In particular, it has the merit that it is dissolved quickly and does not cause an environmental problem when discharged.

In other words, the stabilized isothiazolone solution may be extensively used in the following fields: germicidal agents, sanitary aids, purifier, deodorizer, soap in the form of liquid or powder, anti-oil and anti-greasing agents, chemical products for the treatment of foods, daily chemical products, food protectives, protectives for animal feeds, wood protectives, dyes, lazures, flavoring agents, medical preservatives including hospital, metal agents, dyeing solutions, cooling water, air purifier, petroleum manufacture, paper-treatment, anti-slime agent at a paper mill, petroleum products, adhesives, fibers, paint slurry, latex, treatment for leather articles, petroleum fuels, laundry disinfectants, blending feeds for farming, ink, mining, non-woven fabric, petroleum reservoirs, paste material, rubber, sugar refining, tobacco, swimming pool, cosmetics, commodities for toilet, pastes, plastics, cardboard, pharmaceuticals, chemical toilet paper, household laundries, additives for diesel fuel, wax, cork, lubricants, commodities for construction, blending or polishing agents for concrete; it may also be used in the area that is contaminated or contamination-vulnerable by bacteria, fungi or algae and in the places containing organic materials and water where undesirable microorganisms may grow.

The present invention is explained in more detail by the following illustrative examples. It is not intended that the scope of the claims be limited to these examples.

Isothiazolone solutions obtained from the following examples and comparative example were respectively left in an isothermal bath at 65° C. to measure thermal stabilities. The degree of degradation was measured by high performance liquid chromatography (HPLC). The thermal stability was measured at 65° C. In general, the thermal stability measured at 65° C. during one week corresponds to that measured at 25° C. during 7 months.

EXAMPLE 1

Stabilized isothiazolone solution was prepared by blending 25 wt % of an isothiazolone mixture comprising 5-chloro-2-methyl-4-isothiazolin-3-one chlorate and 2-methyl-4-isothiazolin-3-one chlorate, 75 wt % of the aqueous solution comprising 98 wt % sulfuric acid, without using metal salt stabilizer. The method of observing precipitates in the prepared solution was by naked eye viewing over time. The results of residual contents (%) and formed precipitates with the lapse of time are represented in Table 1.

TABLE 1

| | Residual content and precipitation over time. | | | | | | | | | |
|---|---|---|---|---|---|---|---|---|---|---|
| Term (day) | Beginning | $7^{th}$ | $10^{th}$ | $14^{th}$ | $17^{th}$ | $24^{th}$ | $27^{th}$ | $37^{th}$ | $41^{st}$ | $44^{th}$ | $50^{th}$ |
| Residual contents (%) | 100 | 100 | 100 | 100 | 100 | 100 | 100 | 100 | 98 | 96 | 92 |
| Precipitates | None | None | None | None | None | None | None | None | None | None | None |

EXAMPLE 2

Stabilized isothiazolone solution was prepared by blending 25 wt % of 4,5-dichloro-2-methyl-4-isothiazolin-3-one, 75 wt % of the aqueous solution comprising 98 wt % sulfuric acid, without using metal salt stabilizer. The method of observing precipitates in the prepared solution was by naked eye viewing over time. The results of residual contents (%) and formed precipitates with the lapse of time are represented in the following Table 2.

TABLE 2

Residual content and precipitation over time.

| Term (day) | Beginning | $2^{nd}$ | $7^{th}$ | $10^{th}$ | $15^{th}$ | $17^{th}$ | $20^{th}$ | $27^{th}$ |
|---|---|---|---|---|---|---|---|---|
| Residual contents (%) | 100 | 100 | 100 | 100 | 100 | 100 | 100 | 100 |
| Precipitates | None | None | None | None | None | None | None | None |

EXAMPLE 3

Stabilized isothiazolone solution was prepared by blending 25 wt % of a mixture of 5-chloro-2-methyl-4-isothiazolin-3-one chlorate and 2-methyl-4-isothiazolin-3-one chlorate, 65 wt % of the aqueous solution comprising 98 wt % sulfuric acid, and 10 wt % of deionized water, without using metal salt stabilizer. The results of residual contents (%) with the lapse of time are represented in the following Table 3.

TABLE 3

Residual contents over time.

| Term (day) | Beginning | $2^{nd}$ | $7^{th}$ | $10^{th}$ | $15^{th}$ | $17^{th}$ | $20^{th}$ | $27^{th}$ |
|---|---|---|---|---|---|---|---|---|
| Residual contents (%) | 100 | 100 | 100 | 100 | 100 | 100 | 94 | 91 |

EXAMPLE 4

Stabilized isothiazolone solution was prepared by blending 25 wt % of a mixture of 5-chloro-2-methyl-4-isothiazolin-3-one chlorate and 2-methyl-4-isothiazolin-3-one chlorate, 52 wt % of the aqueous solution comprising 98 wt % sulfuric acid, and 23 wt % of phosphoric acid, without using metal salt stabilizer. The results of residual contents (%) with the lapse of time are represented in the following Table 4.

TABLE 4

Residual contents over time.

| Term (day) | Beginning | $4^{th}$ | $5^{th}$ | $6^{th}$ | $7^{th}$ | $8^{th}$ |
|---|---|---|---|---|---|---|
| Residual contents (%) | 100 | 100 | 100 | 100 | 100 | 97 |

EXAMPLE 5

In order to measure the stability of isothiazolone solution of high concentration, isothiazolone solution was prepared by blending 32 wt % of a mixture of 5-chloro-2-methyl-4-isothiazolin-3-one chlorate and 2-methyl-4-isothiazolin-3-one chlorate, 68 wt % of the aqueous solution comprising 98 wt % sulfuric acid, without using metal salt stabilizer, and the presence of precipitates in the prepared solution was observed by naked eye with the lapse of time. The results of active ingredient contents (wt %) and formed precipitates with the lapse of time are represented in the following Table 5.

TABLE 5

Residual content and precipitation over time.

| Term (day) | Beginning | $7^{th}$ | $14^{th}$ | $21^{st}$ | $28^{th}$ | $35^{th}$ | $42^{nd}$ | $49^{th}$ |
|---|---|---|---|---|---|---|---|---|
| Contents (wt %) | 18.2 | 18.1 | 18.4 | 18.2 | 18.5 | 18.1 | 17.9 | 17.9 |
| Precipitates | None | None | None | None | None | None | None | None |

The data in Table 5 indicates that the stabilized isothiazolone solution is very stable despite of containing 18 wt % or more of active ingredient. In Table 5, the reason why the contents of the active ingredient between 14th and 28th is higher than that in the beginning is that water is evaporated because the stability test in this example is carried out isothermally at 65° C.

EXAMPLE 6

Isothiazolone solution was prepared by blending 2 wt % of a mixture of 5-chloro-2-methyl-4-isothiazoline chlorate and 2-methyl-4-isothiazolin-3-one chlorate, 2 wt % of the aqueous solution comprising 98 wt % sulfuric acid, and 96 wt % of deionized water, without using metal salt stabilizer. The results of residual contents (%) under 50° C. thermostable condition with the lapse of time are represented in the following Table 6.

TABLE 6

Residual contents over time.

| Term (day) | Beginning | $1^{st}$ | $2^{nd}$ | $3^{rd}$ | $4^{th}$ | $5^{th}$ |
|---|---|---|---|---|---|---|
| Residual contents (%) | 100 | 100 | 100 | 100 | 97 | 96 |

EXAMPLE 7

Isothiazolone solution was prepared by blending 10 wt % of a mixture of 5-chloro-2-methyl-4-isothiazoline chlorate and 2-methyl-4-isothiazolin-3-one chlorate, 30 wt % of the aqueous solution comprising 98 wt % sulfuric acid, and 60 wt % of deionized water, without using metal salt stabilizer. The results of residual contents (%) under 50° C. isothermal condition with the lapse of time are represented in the following Table 7.

TABLE 7

Residual contents over time.

| Term (day) | Beginning | $2^{nd}$ | $7^{th}$ | $10^{th}$ | $15^{th}$ | $17^{th}$ | $20^{th}$ | $27^{th}$ |
|---|---|---|---|---|---|---|---|---|
| Residual contents (%) | 100 | 100 | 100 | 100 | 100 | 96 | 91 | 85 |

Comparative Example

Isothiazolone solution was prepared by blending 14 wt % of an isothiazolone mixture comprising 5-chloro-2-methyl- 4-isothiazolin-3-one chlorate and 2-methyl-4-isothiazolin-3-one chlorate in a weight ratio of 3:1 and 10 wt % of metal nitrate as stabilizer. The results of residual contents (%) with the lapse of time are represented in the following Table 8.

TABLE 8

Residual contents over time.

| Term (day) | Begin-ning | $2^{nd}$ | $7^{th}$ | $10^{th}$ | $14^{th}$ | $17^{th}$ | $24^{th}$ | $27^{th}$ |
|---|---|---|---|---|---|---|---|---|
| Residual contents (%) | 100 | 100 | 100 | 100 | 100 | 100 | 98 | 93 |

The data in Tables 1 to 8 indicate that both the stabilized isothiazolone solution of the present invention and the conventional isothiazolone solution using metal salt stabilizer remain stable for a long period. However, the conventional isothiazolone solution using metal salt stabilizer can contain at most about 14 wt % of active isothiazolone, while the stabilized isothiazolone solution of the present invention may contain active isothiazolone more than 18 wt % as shown in the Example 5.

Test 1. Test of Dissociation

In order to measure the speed of dissociation of the stabilized isothiazolone solution of the present invention in water, isothiazolone solutions prepared in Example 1 and the comparative example were respectively poured into deionized water such that the concentrations of active isothiazolone was 100 ppm, and the residual contents (ppm) with the lapse of time were measured. The results are represented in the following Table 9.

TABLE 9

Residual over time.

| Term (day) | Beginning | $1^{st}$ | $2^{nd}$ | $3^{rd}$ | $4^{th}$ | $5^{th}$ |
|---|---|---|---|---|---|---|
| Example 1 | 100 | 96 | 92 | 92 | 90 | 89 |
| Comparative example | 100 | 100 | 100 | 100 | 100 | 100 |

The results in Table 9 indicate that the stabilized isothiazolone solution of the present invention was dissociated in water more rapidly than isothiazolone solution using metal salt stabilizer. The above result means that the isothiazolone solution of the present invention is less likely to induce an environmental problem than that of comparative example, because its medicinal efficacy sustains for a certain period of time and it thereafter dissociates rapidly.

Test 2. MIC Test Against Microorganisms

In order to measure the effect of the stabilized isothiazolone solution of the present invention, isothiazolone solutions prepared in the example 1 and comparative example were respectively poured into deionized water such that the concentrations of active isothiazolone amount to 14 wt %, and the test of MIC (minimum inhibitory concentration) against microorganism was carried out. The results were represented in the following Table 10.

MIC test was carried out in the following manner: Isothiazolone solutions of the Example 1 and comparative example were diluted by double continue dilution method using 96 multi-well plates, then microorganisms were added to a plate in concentration of 10,000 CFU/ml, plates were incubated at 30° C. for 48 hours, and the growth of microorganisms were determined by naked eye on the basis of turbidity. The media used in this test Tryptic Soy Broth (Difco Co.) for bacteria and Potato Dextrose Broth (Difco Co.) for fungi. The strains used in this test were *Staphylococcus aureus* ATCC 6538, *Escherichia coli* ATCC 11229, *Pseudomonas aeruginasa* ATCC 15442, *Pseudomonas oleoverans* ATCC 8062, *Aspergillus niger* ATCC 9642, *Rhizopus oryzae* ATCC 10404, *Pullularia pullulans* ATCC 9384.

TABLE 10

| | MIC concentration (ppm) | |
|---|---|---|
| The used strains | Example 1 | Comparative example |
| *Staphylococcus aureus* ATCC 6538 | 15 | 15 |
| *Escherichia coli* ATCC 11229 | 30 | 30 |
| *Pseudomonas aeruginasa* ATCC 15442 | 30 | 30 |
| *Pseudomonas oleoverans* ATCC 8062 | 15 | 15 |
| *Aspergillus niger* ATCC 9642 | 15 | 15 |
| *Rhizopus oryzae* ATCC 10404 | 15 | 15 |
| *Pullularia pullulans* ATCC 9384 | 15 | 15 |

The result of Table 10 indicates that both the stabilized isothiazolone solution of the present invention and the conventional isothiazolone solution have excellent sterilizing effect against microorganism, and that the degrees of the sterilization of both solutions are comparable.

As explained above, the present invention has the effects of stabilizing the active ingredient for a long term without forming precipitates in contrast to the conventional metal salt stabilizer and, if necessary, preparing a stabilized isothiazolone solution of high concentration. In addition, the conventional metal salt stabilizer may form nitrosamine by products from nitrite ion derived from metal nitrate ion under acidic condition. The present invention can stabilize isothiazolone solution without using metal salt stabilizer thereby preventing the formation of nitrosamine byproducts.

Further, since isothiazolone solution prepared in accordance with the present invention does not contain metal ion, it prevents heavy metals such as $Cu^{2+}$ from being discharged to the environment, and prevents ions such as $Mg^{2+}$ from binding to the ions contained in industrial water. These ions illustratively such as $PO_4^{3-}$ and $CO_3^{2-}$ react to form Hard Scale. Thus, isothiazolone solution of the present invention does not induce secondary environmental pollution and is able to be effectively used in the field of water treatment where a Hard Scale is a serious problem.

The patents and references cited herein are indicative of the skill in the art. These patents and references are incorporated herein by reference to the same extent as if each individual patent or reference was specifically incorporated by reference.

The foregoing description is illustrative of particular embodiments of the invention, but is not meant to be a limitation upon the practice thereof. The following claims, including all equivalents thereof, are intended to define the scope of the invention.

What is claimed is:

1. A stabilized isothiazolone composition comprising (a) an isothiazolone compound, wherein the isothiazolone compound is a mixture of 5-chloro-2-methyl-4-isothiazolin-3-one and 2-methyl-4-isothiazolin-3-one in the weight ratio of 50:50–99:1; (b) sulfuric acid alone or in combination with a phosphorus containing strong acid stabilizer; and (c) a solvent.

2. A method of stabilization of isothiazolone, comprising the step of: blending a stabilizer solution, wherein the stabilizer solution is sulfuric acid alone or in combination with a phosphorus containing strong acid, with an isothiazolone, wherein the isothiazolone compound is a mixture of 5-chloro-2-methyl-4-isothiazolin-3-one and 2-methyl-4-isothiazolin-3-one in the weight ratio of 50:50–99:1.

3. The stabilized isothiazolone composition according to claim 1, wherein the isothiazolone composition is 0.1–40 wt % of the mixture of 5-chloro-2-methyl-4-isothiazolin-3-one and 2-methyl-4-isothiazolin-3-one in the weight ratio of 50:50–99:1, 0.1–99 wt % of stabilizer, and 99.8 wt % or less of solvent.

* * * * *